US006890544B2

(12) United States Patent
McCadden

(10) Patent No.: US 6,890,544 B2
(45) Date of Patent: May 10, 2005

(54) GEL COMPOSITION FOR THE TOPICAL TREATMENT OF POISON IVY AND OTHER FORMS OF CONTACT DERMATITIS

(76) Inventor: Michael E. McCadden, 121 Whitebridge Meadows La., St. Louis, MO (US) 63141

(*) Notice: Subject to any disclaimer, the term of this patent is extended or adjusted under 35 U.S.C. 154(b) by 0 days.

(21) Appl. No.: 10/292,251

(22) Filed: Nov. 12, 2002

(65) Prior Publication Data

US 2003/0077304 A1 Apr. 24, 2003

Related U.S. Application Data

(63) Continuation of application No. 09/652,811, filed on Aug. 31, 2000, now Pat. No. 6,479,058.
(60) Provisional application No. 60/152,068, filed on Sep. 2, 1999.

(51) Int. Cl.$^7$ .............................. A61K 7/00; A61K 7/48; A61K 9/00
(52) U.S. Cl. .................... 424/401; 424/78.05; 514/862; 514/871
(58) Field of Search .............................. 424/401, 78.05; 514/862, 871

(56) References Cited

U.S. PATENT DOCUMENTS

| 4,569,935 A | 2/1986 | Rosenberg et al. |
| 5,110,809 A | 5/1992 | Wang et al. |
| 5,219,877 A | 6/1993 | Shah et al. |
| 5,478,814 A | 12/1995 | Packman |
| 5,883,085 A | * 3/1999 | Blank et al. ................. 514/159 |
| 5,972,920 A | 10/1999 | Seidel |
| 6,391,282 B1 | 5/2002 | Dugger, III |

FOREIGN PATENT DOCUMENTS

| CN | 1095615 A | 11/1994 |
| CN | 1111984 A | 11/1995 |
| EP | 173478 A1 | 3/1986 |
| WO | WO 92/14472 A1 | 9/1992 |
| WO | WO 97/27862 A1 | 8/1997 |

OTHER PUBLICATIONS

Martin H. Wortzel A Double–Blind Study Comparing the Superiority of a combination Antifungal (Clotrimazole)/Steroidal (Betamethasone Dipropionate) Product, CUTIS, vol. 30, (Aug. 1982) pp.258–261.
G. V. Jaffe et al. "An Open Trial of Clotrimazole Plus Hydrocortisone Cream in the Treatment of Napkin Dermatitis in General Practice" Pharmatherapeutica, vol. 4, No. 5 (1985) pp. 314–318.
Richard E. Stoughton "Are Generic Formulations Equivalent to Trade Name Topical Glucocorticoids?" Archives of Dermatology, vol. 123 (Oct. 1987) pp. 1312–1314.
Richard E. Soughton "Bioassay System for Formulations of Topically Applied Glucocorticosteroids" Archives of Dermatology, vol. 106 (Dec. 1972) pp. 825–827.

David B. Jackson et al. "Bioequivalence (bioavailability) of General Topical Corticosteroids" Journal of the American Academy of Dermatology, vol. 20, No. 5, Pt. 1 (May 1989) pp. 791–796.
Cynthia A. Guzzo et al. "Chapter 64, Dermatological Pharmacology" Goodman & Gilman's The Pharmacological Basis of Therapeutics, 9th Ed., McGraw–Hill (1996) pp. 1593–1598.
G. S. Shankland et al. "Comparative in–vitro Activity of Clortimazole and a Clotrimazole/hydrocortisone Combination in the Treatment of Experimental Dermatophytosis in Guinea Pigs" Journal of Antimicrobial Chemotherapy, vol. 25 (1990) pp. 825–830.
Roger C. Cornell et al. "Correlation of the Vasoconstriction Assay and Clinical Activity in Psoriasis" Arch Dermatol, vol. 121 (Jan. 1985) pp. 63–67.
Thomas B. Fitzpatrick et al. Dermatology In General Medicine, vol. II, 4th Ed., McGraw–Hill, Inc., (1993) pp. 2444–2447 and 2847.
E.G.V. Evans et al. "Does Naftifine Have Anti–Inflammatory Properties? A Double–blind Comparative Study With 1% Clotrimazole/1% Hydrocortisone in Clinically Diagnosed Fungal Infection of the Skin" British Journal of Dermatology, vol. 29 (1993) pp. 437–442.
Steven K. Hebel et al. "Drug Facts and Comparisons" Facts and Comparisons, St. Louis, A Wolters Kluwer Company (Jan. 2000) pp. ii, 1658, 1659,1684.
Sandra Levy "Latest Switch—Lamisil—Offers to Get it Done Faster" Drug Topics, Apr. 19, 1999, pp. 72.
A. W. McKenzie et al. "Method for Comparing Percutaneous Absorption of Steroids" Archive of Dermatology, vol. 86, (1962) pp. 608–610.
Virgil A. Place et al. "Precise Evaluation of Topically Applied Corticosteroid Potency" Archives of Dermatology, vol. 101 (May 1970) pp. 531–537.
H. Irving Katz et al. "SCH 370 (Clotirmazole–Betamethasone Dipropionate) Cream in Patients with Tinea Cruris or Tinea Corporis" vol. 34 (Aug. 1984) pp. 183–188.
Paul Walsh et al. "Schering, Lotrisone" Physicians' Desk Reference PFR 55ed 2001, pp. 2912–2914.
A. R. W. Bowring et al. "The Treatment of Napkin Dermatitis: a Double–Blind Comparison of Two Steroid–Antibiotic Combinations" Pharmatherapeutica, vol. 3, No. 9 (1984) pp. 613–617.
Richard E. Soughton "Vasoconstrictor Activity and Percutaneous Absorption of Glucocorticosteroids"Archives of Dermatology, vol. 99 (Jun. 1969) pp. 753–756.
Facts and Comparisons, on Aveeno® anti–itch, by Rydelle, revised May 1992, p. 564a.
Physician's Desk Reference, on Caldry®, by Pfizer, obtained from PDR on–line, (1995).
"USP 24, NF 19" U.S. Pharmacopeia & National Formulary, The United States Pharmacopeial Convention, Inc. 12601 Twinbrook Parkway, Rockville, MD (1999) pp. 273–274, 1768–1769.

* cited by examiner

*Primary Examiner*—Thurman K. Page
*Assistant Examiner*—Mina Haghighatian
(74) *Attorney, Agent, or Firm*—Senniger Powers

(57) ABSTRACT

Composition for topical administration comprising (a) a corticosteroid, and (b) a drying agent.

19 Claims, No Drawings

GEL COMPOSITION FOR THE TOPICAL TREATMENT OF POISON IVY AND OTHER FORMS OF CONTACT DERMATITIS

REFERENCE TO RELATED APPLICATIONS

This application is a continuation of U.S. Ser. No. 09/652,811, filed Aug. 31, 2000 now U.S. Pat. No. 6,479,058, which claims priority from provisional application Ser. No. 60/152,068, filed Sep. 2, 1999.

BACKGROUND OF THE INVENTION

The present invention relates to a composition for the treatment of rashes, dermatoses or skin eruptions, which are known to be treated topically to improve or favorably alter the disease condition. Such rashes, dermatoses or skin eruptions include acute, inflammatory reactions of the skin caused by an allergic or irritant reaction (such as that caused by poison ivy, poison oak or poison sumac, or other forms of allergic or irritant contact dermatitis), other forms of eczema, lichen simplex chronicus, rashes, dermatoses or skin eruptions of a chronic nature (e.g. seborrheic dermatitis, psoriasis, atopic dermatitis) or caused by infection, irritation or aggravation of another condition such as occurs with acne, and other rashes, dermatoses or skin eruptions.

Contact dermatitis may be produced by primary irritants or allergic sensitizes. Irritant contact dermatitis is a nonallergic reaction of the skin caused by exposure to irritating substances. Any person would react to an irritant if the concentration and duration of contact were sufficient. Most primary irritants are chemical substances, although physical and biologic (infectious) agents may produce the same reaction. Irritants account for 80% of occupational contact dermatitis and also cause the most frequent type of nonindustrial contact reaction. Allergic contact dermatitis is a manifestation of delayed hypersensitivity and results from the exposure of sensitized individuals to contact allergens. Poison ivy and poison oak induce sensitization in more than 70% of the population, thereby causing allergic contact dermatitis (Arndt, Kenneth A., *Manual of Dermatologic Therapeutics*, 5$^{th}$ edition, 1995, Little, Brown and Co., page 49).

Irritants will cause an inelastic and stiff-feeling skin, discomfort due to dryness, pruritus secondary to inflammation, and pain due to fissures, blisters, and ulcers. Mild irritants produce erythema, microvesiculation, and oozing that may be indistinguishable from allergic contact dermatitis. Chronic exposure to mild irritants or allergens results in dry, thickened, and fissured skin. Strong irritants cause blistering, erosion, and ulcers of the skin. Allergic contact dermatitis, in its mild form, is similar in appearance to the irritant eruption. A more typical allergic contact reaction will consist of grouped or linear tense vesicles and blisters. If involvement is severe there may be marked edema, particularly of the face and in the periorbital and genital areas.

A variety of methods exist for treating contact dermatitis, including topical corticosteroids, aluminum acetate (Burow's solution), soothing shake lotions (e.g. calamine lotion), oral antihistamines, and systemic corticosteroids. Individually these therapies do not bring rapid relief of all the symptoms of pruritus (itch), the inflammation of the dermatitis, as well as vesiculation and oozing. Usually combination therapy is preferred.

Systemic corticosteroids will cure most cases of contact dermatitis, no matter how severe. But initial dosage should be 60 mg of prednisone daily (or an equivalent strength of another form of corticosteroid), and the course should be no shorter then 2–3 weeks. There are many contraindications to corticosteroid treatment. Absolute contraindications include ocular herpes simplex and untreated tuberculosis. Relative contraindications include acute or chronic infections, pregnancy, diabetes mellitus, hypertension, peptic ulcer, osteoporosis, psychotic tendencies, renal insufficiency, congestive heart failure, and recent intestinal anastomoses (Arndt, Kenneth A., *Manual of Dermatologic Therapeutics*, 5$^{th}$ edition, 1995, Little, Brown and Co., page 309). There are many common corticosteroid complications, including psychiatric disorders, pseudotumor cerebri, osteoporosis with spontaneous fractures, aseptic necrosis of bone, myopathy, glaucoma, cataracts, fatty infiltration of the liver, intestinal perforation, pancreatitis, peptic ulceration, hypertension, sodium and fluid retention, hypokalemic alkalosis, atherosclerosis, immunosuppression, increased incidence of infections, suppression of the hypothalamic-pituitary-adrenal axis, growth failure, and inhibition of wound healing. So, while the clinical results from systemic corticosteroid use are encouraging, a more rapid and complete clinical response with less risk of side effects is desired.

Topical corticosteroids will eradicate a case of contact dermatitis, but will not rapidly stop new vesicles from forming or dry up oozing, weeping patches and vesicles rapidly. While these results are encouraging, a more rapid and complete clinical response is desired.

Soothing lotions (e.g. calamine lotion) and other drying agents such and aluminum acetate (Burow's solution) will dry oozing, weeping patches, vesicles and erosions. But when used alone they typically do not provide relief from the inflammation caused by the dermatitis. Again, while these results are encouraging, a more rapid and complete clinical response is desired.

None of the above agents provide rapid drying of a moist, oozing rash while helping to absorb further moisture and keep the skin dry, and at the same time treat the contact dermatitis.

There are several other papulosquamous skin diseases that can present and behave in a similar fashion to contact dermatitis. These include all other forms of eczema, lichen simplex chronicus, rashes, dermatoses or skin eruptions of a chronic nature (e.g. seborrheic dermatitis, psoriasis, atopic dermatitis), and others. All of these conditions can present with a rash that can become moist, weeping, and quite irritated. The rashes can also become secondarily infected. Current therapeutic options do not always clear these conditions as rapidly as desired.

SUMMARY OF THE INVENTION

Among the objects of the present invention, therefore, is the provision of a composition for topical treatment of rashes, dermatoses and skin eruptions, the provision of such a composition which is easily applied to the skin, the provision of such a composition which contains a corticosteroid of the appropriate potency for the condition being treated, the provision of such a composition which promotes rapid drying of moist areas and coats the skin with the drying agent for protection and healing, especially moist exudative rashes and/or rashes in moist areas.

Briefly, therefore, the present invention is directed to a composition for topical administration comprising (a) a corticosteroid, and (b) a drying agent.

These and other objects of the present invention will be more fully understood in the light of the description set forth below.

DETAILED DESCRIPTION OF THE PREFERRED EMBODIMENTS

The composition of the present invention may be in the form of a solution, spray, lotion, cream, gel or ointment. The preferred form of the composition depends upon the condition being treated and the desired therapeutic effect. For example, treatment of a moist, acutely inflamed rash is preferably treated with a lotion, whereas treatment of a chronic dry patch is often treated more effectively with a cream or ointment. In general, the effectiveness of the composition is directly related to the form of the composition with ointment forms of corticosteroid being stronger than gels, gels being stronger than creams, creams being stronger than lotions and solutions. For example, ointment preparations of the same corticosteroid in the same concentration are generally stronger than the cream preparation.

The lotions of the present invention include liquid suspensions and dispersions. Solid-in-liquid suspensions are preparations of finely divided, undissolved drugs or other particulate matter dispersed in liquid vehicles. These suspensions require shaking before application to ensure uniform distribution of solid in the vehicle. Liquid-in-liquid dispersions generally contain a higher water content than cream emulsions and are pourable. Lotions provide a protective, drying, and cooling effect and may act as a vehicle for other agents. The addition of alcohol increases the cooling effect. If an astringent, such as aluminum is present, it will precipitate protein and dry and seal exudating surfaces.

In a preferred embodiment, the composition of the present invention is a shake lotion containing a solid-in-liquid suspension or a liquid-in-liquid dispersion. For example, the shake lotion may be formed by combining a corticosteroid with a solid-in-liquid suspension or liquid-in-liquid emulsion drying lotion. In this embodiment, such compositions preferably contain at least about 15% by weight water, more preferably at least about 20%, still more preferably at least about 30%, and still more preferably about 40% to about 60% by weight water but no emulsifier. Exemplary water-based, solid-in-liquid suspensions and liquid-in-liquid emulsions include calamine lotions.

In general, preferred compositions of the present invention contain up to about 5% by weight of a corticosteriod, up to about 60% by weight drying agent, one or more optional ingredients (for example, one or more anti-itch agents; anti-foaming agents; buffers, neutralizing agents, and agents to adjust pH; coloring agents and decoloring agents; emollients; emulsifying agents, emulsion stabilizers and viscosity builders; humectants; odorants; preservatives, antioxidants, and chemical stabilizers; solvents; and thickening, stiffening, and suspending agents), and a balance of water or solvent.

Vehicles

Topical therapy may be delivered by any of various vehicles, typically solutions, sprays, lotions, gels, creams, and ointments, progressing in order from least to most hydrating and conversely, most to least drying. Alternatively, the composition may be delivered via a liposome, nanosome, rivosome, or nutri-diffuser vehicle.

The chemical composition of the vehicle may affect the bioavailability and thus, the therapeutic effectiveness of the composition. In general, acute inflammation is treated with aqueous drying preparations, and chronic inflammation is treated with hydrating preparations. Powder-in-water suspension type lotions, solutions (medications dissolved in a solvent) and gels are for hairy and intertriginous areas. Oil-in-water emulsion type lotions, creams and ointments tend to be more absorbable and more effective hydrating agents, appropriate for dry scaly eruptions, but are greasy and therefore often undesirable. In general, solutions, powder-in-water suspension type lotions, lotions and gels are preferred and, for many applications such as the treatment of contact dermatitis, powder-in-water lotions (sometimes referred to as "shake lotions") are particularly preferred.

Preferred vehicles of the present invention include calamine containing lotions and gels. Calamine lotions are preferably shake-lotions containing calamine, zinc oxide, glycerin, thickening agent(s), water and one or more optional ingredients identified as additional agents elsewhere herein. Calamine gels generally contain the same ingredients as the calamine lotions and are, for example, gels of water, acetone, alcohol, or propylene glycol thickened with organic polymers such as carbopols. Preferred lotions typically include calamine (about 2% to about 20% by weight, preferably about 4% to about 15% by weight, more preferably about 6% to about 10% by weight), zinc oxide (about 2% to about 20% by weight, preferably about 4% to about 15% by weight, more preferably about 6% to about 10% by weight), glycerin (about 1% to about 10%, preferably about 2% to about 5% by weight), bentonite magma (about 1 to about 30% by weight, preferably about 2% to about 25% by weight), and calcium hydroxide in sterile water (to make 100% by weight). Preferred optional ingredients additionally include talc (about 2% to about 30% by weight, preferably about 5% to about 15% by weight, more preferably about 10% by weight), peanut oil (about 20% to about 80% by weight, preferably about 25% to about 75% by weight, more preferably about 50% by weight), phenol (up to about 5% by weight), alcohol (up to about 50% by weight) and tannic acid (up to about 5% by weight). Calamine gels may additionally include, for example, microcrystalline cellulose gel (about 20% to about 60% by weight, preferably about 30% to about 50% by weight, more preferably about 45% by weight), and carmellose sodium (up to about 5% by weight).

Corticosteroid

The corticosteroid preferably provides the desired therapeutic effect with little or no risk of causing atrophy of the skin, induction of telangieclasia or, in infants, suppression of hypothalamic-pituitary-adrenal axis. The corticosteroid selected and the concentration thereof in the composition, therefore, will depend, at least in part upon the therapeutic application and the vehicle selected. For example, the therapeutic effectiveness of a topical corticosteroid is related to the potency of the drug and its percutaneous penetration. Therapeutic effectiveness is thus significantly affected by the vehicle. For example, the potency of two of the stronger preparations can be modified by alteration of the corticosteroid moiety in one (clobetasol propionate) and optimization of the vehicle in the other (betamethasone dipropionate). Also, small changes in molecular structure related to enhancing the intrinsic activity of the corticosteroid moiety, increasing lipophiliciity to facilitate better skin penetration, and retarding the metabolic inactivation of the molecule result in significant alterations in clinical effectiveness. The corticoseteroid, therefore, may be a high-potency, mid-potency or low-potency corticosteroid. In general, mid-potency and low-potency corticosteroids are preferred and the composition preferably contains at least about 0.0005% and typically up to about 5% by weight of the corticosteriod.

For pediatric patients and for treatment of intertriginous areas in any age group, low potency steroids are generally preferred in view of certain disadvantages of high-potency steroids. Fluorinated steroids such as betamethasone dipropionate and triamcinalone can be cutaneously dangerous to use in intertriginous regions and can cause undesirable effects including skin atrophy, rebound phenomenon and telangiectasia. If applied to large surface areas on infants, they can cause systemic effects with suppression of hypothalamic-pituitary-adrenal axis. Exemplary low-potency steroids (and concentrations expressed as a weight percentage of the composition of the present invention) include:

- hydrocortisone (about 0.1% to about 5%, preferably about 0.25% to about 3.5%, more preferably about 0.5 to about 2.5% by weight);
- hydrocortisone acetate (about 0.1% to about 5%, preferably about 0.25 to about 3.5%, more preferably about 0.5% to about 2.5% by weight);
- cortisone (about 0.1% to about 5%, preferably about 0.25 to about 3.5%, more preferably about 0.5 to about 2.5% by weight);
- prednisone acetate (about 0.025% to about 1.25%, preferably about 0.05% to about 1%, more preferably about 0.125% to about 0.75% by weight);
- prednisone valerate (about 0.025% to about 1.25%, preferably about 0.05% to about 1%, more preferably about 0.125% to about 0.75% by weight);
- prednisolone (about 0.025% to about 1.25%, preferably about 0.05% to about 1%, more preferably about 0.125% to about 0.75% by weight);
- alclometasone dipropionate (about 0.01% to about 0.1%, preferably about 0.025% to about 0.075%, more preferably about 0.05% by weight);
- dexamethasone (about 0.005% to about 1%; preferably about 0.01% to about 0.5%; more preferably about 0.05% to about 0.1% by weight);
- methylprednisolone (about 0.01% to about 5%, preferably about 0.05% to about 2.5%, more preferably about 0.5% to about 1% by weight);
- fluocinolone acetonide (about 0.0025 to about 0.025%, preferably about 0.005% to about 0.0125%, more preferably about 0.01% by weight); and
- desonide (about 0.01% to about 0.1%, preferably about 0.025% to about 0.075%, more preferably about 0.05% by weight).

Some conditions, such as some forms of contact dermatitis, recalcitrant psoriasis, or forms of lichen simplex chronicus will require a mid-potency steroid for effective treatment. Exemplary mid-potency steroids include:

- fluocinolone acetonide (about 0.005% to about 0.075%, preferably about 0.01% to about 0.05%, more preferably about 0.025% by weight);
- hydrocortisone butyrate (about 0.01% to about 1%; preferably about 0.05% to about 0.5%; more preferably about 0.1% by weight);
- prednicarbate (about 0.01% to about 0.5%, preferably about 0.05% to about 0.25%, more preferably about 0.1% by weight);
- hydrocortisone propionate (about 0.01% to about 1%; preferably about 0.05% to about 0.5%; more preferably about 0.1% by weight); and
- hydrocortisone valerate (about 0.01% to about 1%; preferably about 0.05% to about 0.5%; more preferably about 0.2% by weight).

Some cases of contact dermatitis and conditions in non-intertriginous areas and non-pediatric patients require a fluorinated mid-potency steroid or high-potency steroid for effective treatment. Exemplary fluorinated mid-potency steroids and high-potency steroids include:

- flumethasone pivolate (about 0.005% to about 0.1%, preferably about 0.01% to about 0.05%, more preferably about 0.03% by weight);
- clocortolone pivolate (about 0.01% to about 1%, preferably about 0.05% to about 0.5%, more preferably about 0.1% by weight);
- triamcinolone acetonide (about 0.001% to about 1%; preferably about 0.01% to about 0.5%; more preferably about 0.025% to about 0.1% by weight);
- fluticasone propionate (about 0.0005% to about 0.5%; preferably about 0.001% to about 0.1%; more preferably about 0.005% to about 0.05% by weight);
- flurandrenolide (about 0.005% to about 0.5%; preferably about 0.01% to about 0.1%; more preferably about 0.025% to about 0.05% by weight);
- mometasone furoate (about 0.01% to about 0.5%, preferably about 0.05% to about 0.25%, more preferably about 0.1% by weight);
- desoximetasone (about 0.005% to about 1%; preferably about 0.01% to about 0.5%; more preferably about 0.05% to about 0.25% by weight);
- betamethasone (about 0.005% to about 0.5%; preferably about 0.01% to about 0.25%; more preferably about 0.05% to about 0.1% by weight);
- betamethasone dipropionate (about 0.005% to about 0.5%; preferably about 0.01% to about 0.1%; more preferably about 0.05% by weight);
- betamethasone valerate (about 0.01% to about 0.5%, preferably about 0.05% to about 0.25%, more preferably about 0.1% by weight);
- betamethasone propionate (about 0.005% to about 0.5%; preferably about 0.01% to about 0.1%; more preferably about 0.05% by weight);
- betamethasone benzoate (about 0.005% to about 0.5%; preferably about 0.01% to about 0.1%; more preferably about 0.05% by weight);
- diflorasone diacetate (about 0.005% to about 0.5%; preferably about 0.01% to about 0.1%; more preferably about 0.05% by weight);
- fluocinonide (about 0.005% to about 0.5%; preferably about 0.01% to about 0.1%; more preferably about 0.05% by weight);
- halcinonide (about 0.01% to about 0.5%, preferably about 0.05% to about 0.25%, more preferably about 0.1% by weight);
- amcinonide (about 0.01% to about 0.5%, preferably about 0.05% to about 0.25%, more preferably about 0.1% by weight);
- halobetasol propionate (about 0.005% to about 0.5%; preferably about 0.01% to about 0.1%; more preferably about 0.05% by weight); and
- clobetasol propionate (about 0.005% to about 0.5%; preferably about 0.01% to about 0.1%; more preferably about 0.05% by weight).

In general, the relative potency of topical steroids may be determined by a vasoconstrictor assay. Such assays visually measure the amount of vasoconstriction produced by the steroid with the degree of pallor produced after application of the steroid over a period of time increasing with the concentration of the steroid. See, for example, McKenzie et al., Archives of Dermatology, vol. 86, pp. 608–610 (1962);

Stoughton, Archives of Dermatology, vol. 99, pp. 753–756 (1969); Place et al., Archives of Dermatology, vol. 101, pp. 531–537 (1970); Staughton, Archives of Dermatology, vol. 106, pp. 825–827 (1972); Jackson et al., Journal of the American Academy of Dermatology, vol. 20, pp. 791–796 (1989); and Staughton, Archives of Dermatology, vol. 123, pp. 1312–1314 (1987). To some extent, these assays are imprecise due to the variation between observers and other parameters within an individual study. Nevertheless, general trends emerge and the potency of a steroid may be determined by reference to the potency of other steroids which have been classified as low-potency, mid-potency, or high-potency herein. For example, the potency of a steroid may be determined in a vasoconstrictor assay of the type described by these articles with reference to the low-potency, mid-potency and high-potency corticosteroids identified herein with a corticosteroid being considered a low-potency if it produces an amount of vasoconstriction which is equivalent to the amount of vasoconstriction produced by the low-potency steroids disclosed herein. In Fitzpatrick, Thomas, D., et al., *Dermatology in General Medicine*, (4th ed., 1993 McGraw-Hill, Inc., p. 2847), the potency ranking for a number of commonly used corticosteroids is given as determined by double-blind clinical studies and vasoconstrictor assays. In general, the corticosteroids identified as low potency corticosteroids herein fall within Groups 7 and 8 in this ranking, the corticosteroids identified as mid-potency corticosteroids herein fall within Groups 4 and 5 in this ranking and the corticosteroids identified as high-potency steroids herein fall within Groups 1, 2 and 3 of this ranking.

The composition of the present invention may contain each of the above-identified steroids in solution, spray, lotion, cream, gel or ointment form with the corticosteroid selected and the concentration thereof in the composition, depending at least in part, upon the therapeutic application and the vehicle selected.

Drying Agent

The drying agent generally promotes rapid drying of moist areas and coats the skin for protection and healing. In particular, it acts to prevent irritation of the involved area and water loss from the skin layer by forming a physical barrier on the skin. Preferred drying agents include calamine; zinc containing drying agents such as zinc oxide, zinc acetate, zinc stearate and zinc sulfate; copper sulfate; kaolin; potassium permanganate; Burow's aluminum solution; talc; starches such as wheat and corn starch; silver nitrate, and acetic acid. Calamine and zinc oxide are particularly preferred.

In general, the composition of the present invention contains at least about 2.5% by weight and no more than about 60% by weight drying agent. Typically, the composition contains about 5% to about 50% by weight drying agent, and for many applications such as the treatment of contact dermatitis, the composition preferably contains about 7% by weight to about 25% by weight drying agent. The composition may contain a single drying agent, for example, calamine or zinc oxide, or a combination of drying agents, for example, calamine and zinc oxide, calamine and zinc stearate, or calamine and one or more starches. When the composition contains calamine and one or more other drying agents such as zinc oxide, the weight ratio of calamine to the other drying agent(s) is generally about 0.5:1 to about 10:1, respectively. For example, the weight ratio of calamine to zinc-containing drying agents will preferably be about 1:1 to about 3:1, respectively, the weight ratio of calamine to talc will preferably be about 1:1 to about 3:1, respectively, and the weight ratio of calamine to starch drying agent(s) will preferably be about 1:1 to about 10:1, respectively, in compositions containing calamine and one or more other drying agents. Calamine (which is zinc oxide with approximately 0.5% by weight ferric oxide) reduces inflammation, redness and itching, as well as promoting drying of excess oils and fluids; preferably, therefore, the composition includes calamine in an amount between about 7 and 25 weight percent and, more preferably, additionally includes zinc oxide in an amount between 7 and about 25 weight percent. A particularly preferred composition for contact dermatitis comprises calamine (about 7% to about 10% by weight) and zinc oxide (about 7% to about 10% by weight).

Additional Agents

The composition of the present invention preferably additionally comprises an anti-itch agent such as phenol, camphor, menthol, benzocaine, diphenylhydramine or pramoxine. In general, the concentration of these anti-itch agents in the composition will be about 0.3 wt % to about 1 wt % for menthol, camphor and phenol; about 0.5 wt. % to about 20 wt % benzocaine; about 0.1 wt. % to about 20 wt %, more preferably about 0.5 wt % to about 5 wt. %, and still more preferably about 1 wt % to about 2 wt % for diphenylhydramine; and about 0.1 wt. % to about 20 wt %, more preferably about 0.5 wt % to about 5 wt. %, and still more preferably about 1 wt % for pramoxine. When an anti-itch agent is included, particularly if the anti-itch agent is diphenylhydramine or pramoxine, the composition preferably additionally comprises zinc acetate (about 0.01 wt % to about 5 wt. %, more preferably about 0.05 wt. % to about 3 wt. %, and still more preferably about 0.1 wt. % to about 1 wt. % zinc acetate).

The composition of the present invention may also include a wide range of other optional ingredients including, antifoaming agents; buffers, neutralizing agents and agents to adjust pH; coloring agents and decoloring agents; emollients; emulsifying agents; emulsion stabilizers and viscosity builders; humectants; odorants; preservatives, antioxidants, and chemical stabilizers; solvents; and thickening, stiffening and suspending agents. Exemplary antifoaming agents include cyclomethicone, dimethicone (e.g., dimethicone 350) and simethicone. Exemplary buffers, neutralizing agents and agents to adjust pH include ammonium hydroxide, citric acid, diisopropanolamine, hydrochloric acid, lactic acid, monobasic sodium phosphate, sodium citrate, sodium hydroxide, sodium phosphate, triethanolamine, and trolamine. Exemplary emollients include caprylic/capric triglyerides, castor oil, ceteareth-20, ceteareth-30, cetearyl alcohol, ceteth 20, cetostearyl alcohol, cetyl alcohol, cetyl stearyl alcohol, cocoa butter, diisopropyl adipate, glycerin, gyceryl monooleate, glyceryl monostearate, glyceryl stearate, isopropyl myristate, isopropyl palmitate, lanolin, lanolin alcohol, hydrogenated lanolin, liquid paraffins, linoleic acid, mineral oil, oleic acid, white petrolatum, polyethylene glycol, polyoxyethylene glycol fatty alcohol ethers, polyoxypropylene 15-stearyl ether, propylene glycol stearate, squalane, steareth-2 or -100, stearic acid, stearyl alcohol and urea. Exemplary emulsifying agents include aluminum starch octenylsuccinate, ammonium hydroxide, amphoteric-9, beeswax, synthetic beeswax, carbomer 934, carbomer 934P, carbomer 940, ceteareth-20, ceteareth-30, cetearyl alcohol, ceteth 20, cetyl alcohol, cholesterol, cyclomethicone, diglycerides, dimethicone (e.g., dimethicone 350), disodium monooleamidosulfosuccinate, NF emulsifying wax, fatty acid pentaerythritol ester, glycerides, glyceryl monooleate, glyceryl monostearate, lanolin, lanolin alcohol, hydrogenated lanolin, magnesium stearate, mineral oil, monoglycerides, polyethylene glycol, PEG 100 stearate, polyethylene glycol 6000 distearate, polyethylene glycol 1000 monocetyl ether, polyethylene glycol monostearate, polyethylene glycol 400 monostearate, polyoxyethylene glycol fatty alcohol ethers, polyoxyl 20 cetostearyl ether, polyoxyl 40 stearate, polysorbate 20, polysorbate 40, polysorbate 60, polysorbate 80, polysorbates, PPG-26 oleate, propylene glycol stearate, quaternium-15, simethicone, sodium laureth sulfate, sodium lauryl sulfate, sorbitan esters, sorbitan monolaurate, sorbitan monooleate, sorbitan monopalmitate, sorbitan monostearate, sorbitan palmitate, sorbitan sesquioleate, steareth-2, steareth-100, stearic acid, stearyl alcohol, triethanolamine and trolamine.

Exemplary emulsion stabilizers and viscosity builders include carbomer 934, carbomer 934P, carbomer 940, cetearyl alcohol, cetostearyl alcohol, cetyl alcohol, cetyl stearyl alcohol, dextrin, diglycerides, disodium edetate, edetate disodium, glycerides, glyceryl monostearate, glyceryl stearate, hydroxypropyl cellulose, monoglycerides, plasticized hydrocarbon gel, polyethylene glycol 300, polyethylene glycol 400, polyethylene glycol 1450, polyethylene glycol 8000, polyethylene glycols, propylene glycol stearate and stearyl alcohol. Exemplary humectants include glycerine, propylene glycol, sorbitol and urea. Exemplary odorants include hypoallergenic perfume, menthol. Exemplary preservatives, antioxidants, and chemical stabilizers include alcohol, benzyl alcohol, butylated hydroxyanisole, butylated hydroxytoluene, butylparaben, calcium acetate, caster oil, chlorocresol, 4-chloro-m-cresol, citric acid, disodium edetate, Dowicil 200 (Dow), edetate disodium, ethoxylated alcohol, ethyl alcohol, glycerin, Glydant Plus (Lonza), 1,2,6-hexanetriol, Kathon CG (Rohm & Haas), Liquid Germall Plus (ISP Sutton Labs), Liquipar (ISP Sutton Labs), methylparaben, parabens, potassium sorbate, propyl gallate, propylene glycol, propylparaben, sodium bisulfite, sodium citrate, sodium metabisulfite, sorbic acid, tannic acid, triglycerides of saturated fatty acids, Ucarcide (Union Carbide), and zinc stearate. Exemplary solvents include alcohol, castor oil, diisopropyl adipate, ethoxylated alcohol, ethyl alcohol, fatty alcohol citrate, glycerin, 1,2,6-hexanetriol, hexylene glycol, isopropyl alcohol, isopropyl myristate, isopropyl palmitate, mineral oil, phosphoric acid, polyethylene glycol 300, polyethylene glycol 400, polyethylene glycol 1450, polyethylene glycol 8000, polyethylene glycol 1000 monocetyl ether, polyethylene glycol monostearate, polyethylene glycol 400 monostearate, polyethylene glycols, polyoxyl 20 cetostearyl ether, polyoxypropylene 15-stearyl ether, polysorbate 20, polysorbate 40, polysorbate 60, polysorbate 80, polysorbates, propylene carbonate, propylene glycol, purified water, and SD alcohol 40, triglycerides of saturated fatty acids. Exemplary thickening, stiffening and suspending agents include aluminum stearate, beeswax, synthetic beeswax, carbomer 934, carbomer 934P, carbomer 940, cetostearyl alcohol, cetyl alcohol, cetyl esters wax, dextrin, glyceryl monostearate, hydroxypropyl cellulose, kaolin, paraffin, petrolatum, polyethylene, propylene glycol stearate, starch, stearyl alcohol, wax, white wax, xanthan gum, and bentonite.

Other agents which may be added to the composition of the present invention include, for example, aloe, arachis oil, benzoic acid, cocoa butter (up to about 70% by weight); coenzyme Q10 (Aubiquinone@), Q10, dimethicone, eucalyptus oil; resorcinol (up to about 5% by weight); retinol; retinyl palmitate; retinyl acetate; fennel extract; whey protein; ceramide; silicone (about 1% to about 50% by weight); alpha-hydroxy acids, beta-hydroxy acids, sorbitol, vitamin A (about 500 International Units per gram to about 300,000 International Units per gram provided, for example, in the form of fish liver oil, cod liver oil or shark liver oil), vitamin B (including panthenol and beta-carotene), vitamin C, vitamin D (about 50 International Units per gram to about 500 International Units per gram), vitamin E (about 20 International Units per gram to about 500 International Units per gram), and vitamin K. Unless otherwise indicated, the composition will generally contain less than about 5% by weight and typically less than about 1% by weight of the above-ingredients.

Treatment/Administration

The composition of the invention is applied topically to the involved area until it has healed. For example, for contact dermatitis a composition containing hydrocortisone (about 1% by weight), calamine (about 8% by weight), zinc oxide (about 8% by weight), glycerin (about 2% by weight), bentonite magma (about 25% by weight) and calcium hydroxide in sterile water (to 100%) is preferably administered two to four times a day for from one day to a week or more until healing occurs.

In one embodiment, the composition of the present invention comprises a nonpainful, soothing agent that will control the contact dermatitis (e.g., a corticosteroid), and that will dry the area rapidly (e.g., calamine). In addition, it can effectively provide fast relief of symptoms and eradication of the contact dermatitis while minimizing the risk of undesirable side effects such as secondary infection caused by the presence of moist, open wounds. For such uses, the composition preferably contains a (i) low-potency steroid such as hydrocortisone, hydrocortisone acetate, alclometasone dipropionate, fluocinolone acetonide, or desonide, and (ii) a drying agent such as a calamine containing lotion or gel. For such uses, the composition more preferably contains a (i) low-potency steroid such as hydrocortisone, alclometasone dipropionate, or desonide, and (ii) a drying agent such as a calamine containing lotion or gel. For such uses, the composition still more preferably contains (i) hydrocortisone, and (ii) a drying agent such as a calamine containing lotion or gel. The concentration of the low-potency steroid in these compositions is preferably about 0.25% to about 3.5% by weight, more preferably about 0.5% to about 2.5% by weight for hydrocortisone and hydrocortisone acetate; preferably about 0.025% to about 0.075% by weight and more preferably about 0.05% for alclometasone dipropionate and desonide; and preferably about 0.005% to about 0.0125% by weight and more preferably about 0.01% by weight for fluocinolone acetonide.

In another embodiment, for conditions such as more severe contact dermatitis, severe seborrhea, recalcitrant psoriasis, or forms of lichen simplex chronicus, the composition will include a mid-potency steroid for more effective treatment. For such uses, the composition preferably contains (i) a mid-potency steroid such as hydrocortisone butyrate, hydrocortisone valerate, or prednicarbate and (ii) a drying agent such as a calamine containing lotion or gel. For such uses, the composition more preferably comprises (i) a mid-potency steroid such as hydrocortisone butyrate or hydrocortisone valerate, and (ii) a drying agent such as a calamine containing lotion or gel. For such uses, the composition still more preferably contains (i) hydrocortisone valerate, and (ii) a drying agent such as a calamine containing lotion or gel. The concentration of hydrocortisone butyrate and hydrocortisone valerate in such compositions is preferably about 0.05% to about 0.5% and more preferably about 0.1 to about 0.2% by weight. The concentration of prednicarbate in such compositions is preferably about 0.01% to about 0.5%, more preferably about 0.05% to about 0.25%, more preferably about 0.1% by weight.

In still another embodiment, for conditions such as very severe, moist weeping vesicular contact dermatitis, severe and recalcitrant seborrhea, severe and recalcitrant psoriasis, or severe and recalcitrant forms of lichen simplex chronicus, the composition will include (i) a fluorinated mid-potency steroid or high-potency steroid for more effective treatment. For such uses, the composition preferably contains (i) a drying agent such as calamine, and (ii) a fluorinated mid-potency or high-potency steroid such as triamcinolone acetonide (about 0.001% to about 1%; preferably about 0.01% to about 0.5%; more preferably about 0.025% to about 0.1% by weight);

fluticasone propionate (about 0.0005% to about 0.5%; preferably about 0.001% to about 0.1%; more preferably about 0.005% to about 0.05% by weight);

flurandrenolide (about 0.005% to about 0.5%; preferably about 0.01% to about 0.1%; more preferably about 0.025% to about 0.05% by weight);

mometasone furoate (about 0.01% to about 0.5%, preferably about 0.05% to about 0.25%, more preferably about 0.1% by weight);

desoximetasone (about 0.005% to about 1%; preferably about 0.01% to about 0.5%; more preferably about 0.05% to about 0.25% by weight);

betamethasone (about 0.005% to about 0.5%; preferably about 0.01% to about 0.25%; more preferably about 0.05% to about 0.1% by weight);

betamethasone dipropionate (about 0.005% to about 0.5%; preferably about 0.01% to about 0.1%; more preferably about 0.05% by weight);

betamethasone valerate (about 0.01% to about 0.5%, preferably about 0.05% to about 0.25%, more preferably about 0.1% by weight);

betamethasone propionate (about 0.005% to about 0.5%; preferably about 0.01% to about 0.1%; more preferably about 0.05% by weight);

betamethasone benzoate (about 0.005% to about 0.5%; preferably about 0.01% to about 0.1%; more preferably about 0.05% by weight);

diflorasone diacetate (about 0.005% to about 0.5%; preferably about 0.01% to about 0.1%; more preferably about 0.05% by weight);

fluocinonide (about 0.005% to about 0.5%; preferably about 0.01% to about 0.1%; more preferably about 0.05% by weight);

halcinonide (about 0.01% to about 0.5%, preferably about 0.05% to about 0.25%, more preferably about 0.1% by weight);

amcinonide (about 0.01% to about 0.5%, preferably about 0.05% to about 0.25%, more preferably about 0.1% by weight);

halobetasol propionate (about 0.005% to about 0.5%; preferably about 0.01% to about 0.1%; more preferably about 0.05% by weight); and clobetasol propionate (about 0.005% to about 0.5%; preferably about 0.01% to about 0.1%; more preferably about 0.05% by weight).

For such uses, the composition more preferably comprises (i) a drying agent such as calamine and (ii) a fluorinated mid-potency or high-potency steroid such as triamcinolone acetonide (about 0.001% to about 1%; preferably about 0.01% to about 0.5%; more preferably about 0.025% to about 0.1% by weight);

fluticasone propionate (about 0.0005% to about 0.5%; preferably about 0.001% to about 0.1%; more preferably about 0.005% to about 0.05% by weight);

mometasone furoate (about 0.01% to about 0.5%, preferably about 0.05% to about 0.25%, more preferably about 0.1% by weight);

desoximetasone (about 0.005% to about 1%; preferably about 0.01% to about 0.5%; more preferably about 0.05% to about 0.25% by weight);

betamethasone (about 0.005% to about 0.5%; preferably about 0.01% to about 0.25%; more preferably about 0.05% to about 0.1% by weight);

betamethasone dipropionate (about 0.005% to about 0.5%; preferably about 0.01% to about 0.1%; more preferably about 0.05% by weight);

betamethasone valerate (about 0.01% to about 0.5%, preferably about 0.05% to about 0.25%, more preferably about 0.1% by weight);

betamethasone propionate (about 0.005% to about 0.5%; preferably about 0.01% to about 0.1%; more preferably about 0.05% by weight);

betamethasone benzoate (about 0.005% to about 0.5%; preferably about 0.01% to about 0.1%; more preferably about 0.05% by weight);

diflorasone diacetate (about 0.005% to about 0.5%; preferably about 0.01% to about 0.1%; more preferably about 0.05% by weight);

fluocinonide (about 0.005% to about 0.5%; preferably about 0.01% to about 0.1%; more preferably about 0.05% by weight);

halobetasol propionate (about 0.005% to about 0.5%; preferably about 0.01% to about 0.1%; more preferably about 0.05% by weight); and clobetasol propionate (about 0.005% to about 0.5%; preferably about 0.01% to about 0.1%; more preferably about 0.05% by weight).

For such uses, the composition still more preferably comprises (i) a drying agent such as calamine, and (ii) a fluorinated mid-potency or high-potency steroid such as triamcinolone acetonide (about 0.001% to about 1%; preferably about 0.01% to about 0.5%; more preferably about 0.025% to about 0.1% by weight);

desoximetasone (about 0.005% to about 1%; preferably about 0.01% to about 0.5%; more preferably about 0.05% to about 0.25% by weight);

betamethasone (about 0.005% to about 0.5%; preferably about 0.01% to about 0.25%; more preferably about 0.05% to about 0.1% by weight);

betamethasone dipropionate (about 0.005% to about 0.5%; preferably about 0.01% to about 0.1%; more preferably about 0.05% by weight);

betamethasone valerate (about 0.01% to about 0.5%, preferably about 0.05% to about 0.25%, more preferably about 0.1% by weight);

betamethasone propionate (about 0.005% to about 0.5%; preferably about 0.01% to about 0.1%; more preferably about 0.05% by weight);

betamethasone benzoate (about 0.005% to about 0.5%; preferably about 0.01% to about 0.1%; more preferably about 0.05% by weight);

diflorasone diacetate (about 0.005% to about 0.5%; preferably about 0.01% to about 0.1%; more preferably about 0.05% by weight);

fluocinonide (about 0.005% to about 0.5%; preferably about 0.01% to about 0.1%; more preferably about 0.05% by weight); and clobetasol propionate (about 0.005% to about 0.5%; preferably about 0.01% to about 0.1%; more preferably about 0.05% by weight).

Preferred exemplary formulation include shake lotions consisting of hydrocortisone (1 wt. %) and calamine lotion (99 wt. %); hydrocortisone (2 wt. %) and calamine lotion (98 wt. %); and hydrocortisone (0.5 wt. %) and calamine lotion (99.5 wt. %) wherein the calamine lotion is prepared by combining the following ingredients in the indicated amounts (or proportions): U.S.P. grade calamine (8 gm), zinc oxide (8 gm), glycerin (2 ml), bentonite magma (25 ml), and calcium hydroxide in sterile water (to 100 ml). More preferably, these formulations include diphenylhydramine HCl (about 1 wt. % to about 2 wt. %) or pramoxine HCl (about 1 wt. %) as an anti-itch agent and zinc acetate (about 0.01 wt. % to about 1 wt. %) with the concentration of calamine lotion (and not the hydrocortisone) being adjusted accordingly.

What is claimed is:

1. A composition for topical administration for the treatment of contact dermatitis, the composition comprising (a) a mid-potency or high-potency corticosteroid, (b) calamine, (c) water, and (d) an anti-itch agent selected from the group consisting of menthol, camphor, phenol, benzocaine, diphenylhydramine and pramoxine, the composition being in the form of a gel and comprising about 0.005% to about 0.1% by weight of the mid-potency or high-potency corticosteroid.

2. The composition of claim 1 wherein the mid potency steroid is selected from the group consisting of fluocinolone acetonide, hydrocortisone butyrate, hydrocortisone propionate, hydrocortisone valerate, and prednicarbate.

3. A composition for topical administration for the treatment of contact dermatitis, the composition consisting essentially of (a) a mid-potency or high-potency corticosteroid, (b) calamine, (c) water, and (d) an anti-itch agent selected from the group consisting of menthol, camphor, phenol, benzocaine, diphenylhydramine, pramoxine and combinations there of in the composition being in the form of a gel and comprising about 0.0005% to about 0.5% by weight of the mid potency or high potency corticosteroid.

4. The composition of claim 3 wherein the mid potency or high potency steroid is selected from the group consisting of flumethasone pivolate, clocortolone pivolate, triamcinolone acetonide, prednicarbate, fluticasone propionate, flurandrenolide, mometasone furoate, desoximetasone, betamethasone, betamethasone dipropionate, betamethasone valerate, betamethasone propionate, betamethasone benzoate, diflorasone diacetate, fluocinonide, halcinoruide, amcinonide, halobetasol propionate, and clobetasol propionate.

5. The composition of claim 4 wherein the composition comprises at least two drying agents, one of the drying agents is calamine, another is zinc oxide and the ratio of calamine to zinc oxide is about 0.5:1 to about 10:1.

6. A composition for topical administration for the treatment of contact dermatitis, the composition comprising (a) a mid-potency or high-potency corticosteroid, (b) calamine, (c) water, and (d) an anti-itch agent selected from the group consisting of menthol, camphor, phenol, benzocaine, diphenylhydramine and pramoxine, the composition being in the form of a gel and comprising at least two drying agents, one of the drying agents being calamine, another being zinc oxide and the ratio of calamine to zinc oxide being about 0.5:1 to about 10:1.

7. The composition of claim 6 wherein the composition comprises about 1 wt. % to about 2 wt. % diphenylhydramine HCl or pramoxine HCl.

8. The composition of claim 4 wherein the composition comprises about 1 wt. % to about 2 wt. % diphenylhydramine HCl or pramoxine HCl.

9. A composition for topical administration for the treatment of contact dermatitis, the composition comprising (a) a mid-potency or high-potency corticosteroid, (b) calamine, (c) water, and (d) an anti-itch agent selected from the group consisting of menthol, camphor, phenol, benzocaine, diphenylhydramine and pramoxine, the composition being in the form of a gel wherein the gel is thickened with an organic polymer.

10. A process for treating contact dermatitis, the process comprising topically applying a composition to the affected area, the composition comprising (a) a mid-potency or high-potency corticosteroid, (b) calamine, (c) water, and (d) an anti-itch agent selected from the group consisting of menthol, camphor, phenol, benzocaine, diphenylhydramine and pramoxine, the composition being in the form of a gel.

11. The process of claim 10 wherein the composition contains about 0.005% to about 0.1% by weight of a mid potency corticosteroid.

12. The process of claim 11 wherein the mid potency steroid is selected from the group consisting of fluocinolone acetonide, hydrocortisone butyrate, hydrocortisone propionate, hydrocortisone valerate, and prednicarbate.

13. The process of claim 10 wherein the composition contains about 0.0005% to about 0.5% by weight of a mid potency or high potency corticosteroid.

14. The process of claim 13 wherein the mid potency or high potency steroid is selected from the group consisting of flumethasone pivolate, clocortolone pivolate, triamcinolone acetonide, prednicarbate, fluticasone propionate, flurandrenolide, mometasone furoate, desoximetasone, betamethasone, betamethasone dipropionate, betamethasone valerate, betamethasone propionate, betamethasone benzoate, diflorasone diacetate, fluocinonide, halcinonide, amcinonide, halobetasol propionate, and clobetasol propionate.

15. The process of claim 14 wherein the composition comprises at least two drying agents, one of the drying agents is calamine, another is zinc oxide and the ratio of calamine to zinc oxide is about 0.5:1 to about 10:1.

16. The process of claim 10 wherein the composition comprises at least two drying agents, one of the drying agents is calamine, another is zinc oxide and the ratio of calamine to zinc oxide is about 0.5:1 to about 10:1.

17. The process of claim 16 wherein the composition comprises about 1 wt. % to about 2 wt. % diphenylhydramine HCl or pramoxine HCl.

18. The process of claim 14 wherein the composition comprises about 1 wt. % to about 2 wt. % diphenylhydramine HCl or pramoxine HCl.

19. The process of claim 10 wherein the gel is thickened with an organic polymer.

* * * * *

UNITED STATES PATENT AND TRADEMARK OFFICE
CERTIFICATE OF CORRECTION

PATENT NO. : 6,890,544 B2
DATED : May 10, 2005
INVENTOR(S) : Michael E. McCadden It is certified that error appears in the above-identified patent and that said Letters Patent is hereby corrected as shown below:

<u>Column 13,</u>
Line 39, "there of in the" should read -- thereof, the --.
Line 50, "halcinoruide," should read -- halcinonide --.

Signed and Sealed this

Thirteenth Day of September, 2005

JON W. DUDAS
*Director of the United States Patent and Trademark Office*